United States Patent [19]

Hartman

[11] 4,443,457
[45] Apr. 17, 1984

[54] AMINOCROTONYLPYRIDINE N-OXIDES USEFUL AS ADJUNCTS TO RADIATION THERAPY

[75] Inventor: George D. Hartman, Lansdale, Pa.

[73] Assignee: Merck & Co., Inc., Rahway, N.J.

[21] Appl. No.: 399,612

[22] Filed: Jul. 19, 1982

[51] Int. Cl.$^3$ .................. C07D 213/89; A61K 31/44
[52] U.S. Cl. ..................................... 424/263; 546/312
[58] Field of Search ........................ 546/312; 424/263

[56] References Cited

PUBLICATIONS

Ainsworth et al., Can. J. Biochem., 10156, pp. 457–461 (1978).
Adams et al., Lancet, pp. 186–188, Jan. (1976).
Olive, P. L., Cancer Res., 39, pp. 4512–4515, Nov. (1979).
Anderson, R. F. et al., "Radiosensitization . . . by Nitropyridium Compounds", Br. J. Cancer, 37, Suppl. III, pp. 103–106 (1978).
Rauth et al., "In Vitro Testing—Radiosensitizers", Chem. Abst. 85:40894F (1976).
Denekamp et al., "Hypoxic Cells Radiosensitizers", Chem. Abst. 82:93112w.
Chin et al., "Screening—Radiosensitizers", Chem. Abst., 89:20966z.

Primary Examiner—Henry R. Jiles
Assistant Examiner—Dale A. Bjorkman
Attorney, Agent, or Firm—Thomas E. Arther; Mario A. Monaco

[57] ABSTRACT

Aminocrotonyl derivatives of 4-nitropyridine N-oxides are disclosed to have activity in increasing the sensitivity of tumor cells to radiation. Also disclosed are methods of preparing such compounds and pharmaceutical compositions including such compounds.

5 Claims, No Drawings

AMINOCROTONYLPYRIDINE N-OXIDES USEFUL AS ADJUNCTS TO RADIATION THERAPY

BACKGROUND OF THE INVENTION

This invention relates to aminocrotonyl derivatives of 4-nitropyridine N-oxides used as sensitizers of tumor cells to therapeutic radiation. It also relates to the process of preparing such compounds starting with 4-nitro-3-fluoropyridine N-oxide and reacting it with amino substituted crotonate ester. In addition, the present invention relates to pharmaceutical compositions comprising such aminocrotonyl pyridine N-oxides and to methods of treatment comprising administering such compounds to patients undergoing radiation treatment to enhance the effectiveness of such treatment.

At the present time, certain other unrelated compounds are in experimental clinical use as radiation sensitizers. However, these compounds—for example, metronidazole and misonidazole—suffer from the drawback that they also cause neurotoxicity which limits their usefulness. The compounds of the present invention are effective radiation sensitizers, but are believed to have a more favorable therapeutic ratio.

DETAILED DESCRIPTION OF THE INVENTION

The composition of the present invention which are useful as radiation sensitizers are derivatives of 4-nitropyridine N-oxide in which the pyridine ring is substituted with a 2-amino (or substituted amino)-1-carboxy (or carboalkoxy)-alken-1-yl radical.

More specifically, the invention relates to derivatives of 4-nitropyridine-N-oxide of the formula

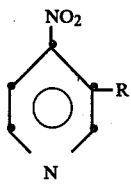

I wherein R is defined as 2-amino (or substituted amino)-1-carboxy (or carboalkoxy)-alken-1-yl radical.

Still more specifically this invention comprises 4-nitropyridine-N-oxides of the formula

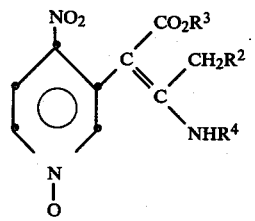

wherein
$R^2$ and $R^3$ is hydrogen, $C_{1-6}$ loweralkyl, hydroxyloweralkyl, or loweralkoxylower alkyl
$R^4$ is hydrogen, $C_{1-6}$ loweralkyl, hydroxylloweralkyl, loweralkoxylloweralkyl.

The substituted 4-nitro pyridine N-oxides described hereinabove are prepared by reaction of 3-fluoro-4-nitropyridine N-oxide with an amino substituted lower alkenyl ester to produce the desired compound in accordance with the equation set forth below;

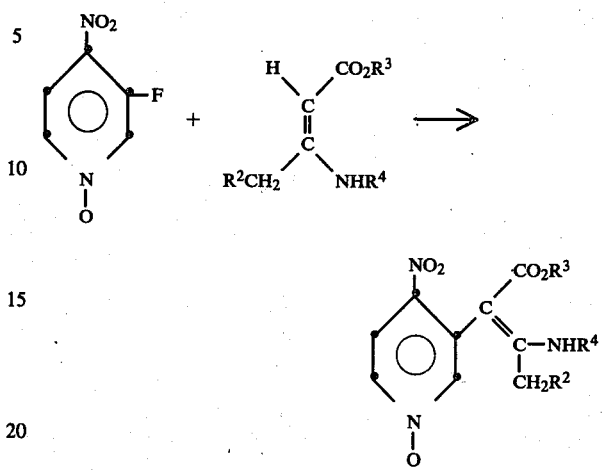

The reaction of the 3-fluoro-4-nitropyridine oxide is carried out by mixing it with an equimolar amount of the selected loweralkenyl ester and maintaining the reaction mixture at a temperature of 25° or heating at a temperature of 50° for a period of 12 hours to 3 days to accelerate the reaction. Progress of the reaction is followed by thin layer chromatography. It is preferred to carry out the reaction in the presence of a solvent for the reactants. Solvents such as loweralkanols e.g. ethanol, n-propanol or isopropanol can be employed for this purpose.

The method of treatment of human patients or domestic animals undergoing radiation treatment of malignant disease processes employs the compounds of the present invention in pharmaceutical compositions that are administered orally or parenterally, or intravenously. The dose employed depends on the radiation protocol for each individual patient. In protocols where the radiation dose is divided into a large number of fractions, the drug can be administered at intervals in the schedule and not necessarily with each radiation treatment. It should be noted that the compounds of the present invention are not intended for chronic administration. In general, the drug is administered from 10 minutes to 5 hours prior to the radiation treatment in a dosage amount of between 0.25 to about 4.0 grams per square meter of body surface approximately equivalent to a dosage of 6 to 100 mg/kg of patient body weight as set forth in the "Nelson Textbook of Pediatrics" Eleventh Edition (1979) p. 31, edited by Vaughan, McKay, Behrman, and Nelson.

The dosage range given is the effective dosage range and the decision as to the exact dosage used must be made by the administering physician based on his judgement of the patient's general physical condition. In determining the dose for the individual patient, the physician may begin with an initial dose of 0.25 g/square meter of body surface to determine how well the drug is tolerated and increase the dosage with each succeeding radiation treatment, observing the patient carefully for any drug side effect. The composition to be administered is an effective amount of the active compound and a pharmaceutical carrier for said active compound.

The dosage form for intravenous administration is a sterile isotonic solution of the drug. Oral dosage forms such as tablets, capsules, or elixirs are preferred.

Capsules or tablets containing 25, 50, 100 or 500 mg of drug/capsule or tablets are satisfactory for use in the method of treatment of our invention.

The following examples are intended to illustrate but do not limit the process of preparation, product, compositions, or method of treatment aspects of the invention.

Preparation of Reactants

Temperatures are expressed in degrees Celsius.

Preparation 1

Methyl 3-(2,3-dihydroxypropyl)amino-2-butenoate (2)

To 5.0 g (0.051 m) methyl-2-butynoate in 25 ml absolute ethanol is added 5.0 g (0.055 m) 2,3-dihydroxypropylamine. This solution is heated at 75°–80° for 18 hours and the solvent is then removed at reduced pressure. The residue oil is chromatographed on silica gel, eluting with 10% methanol/chloroform to afford the desired product as a white solid. m.p. 109°–111°. The yield is 5.6 g (59%).

Preparation 2

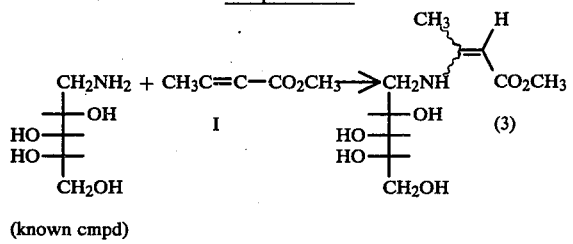

(known cmpd)

Methyl 3-(1-deoxy-1-arabinyl)amino-2-butenoate (3)

To 4.9 g (0.05 m) methylpropiolate in 100 ml dry dimethylsulfoxide is added 6.5 g (0.043 m) 1-amino-1-deoxyarabinitol in one portion. The resulting solution is heated at 70°–75° for 16 hours. The solvent is then removed in vacuo to give a white solid that is triturated with Et₂O. This suspension is filtered to afford the desired product as a white powder, m.p. 162°–4°.

The following examples are intended to illustrate but do not limit the process of preparation, product, compositions, or method of treatment aspects of the invention.

EXAMPLE 1

Methyl 3-(2,3-dihydroxypropyl)amino-2-(4-nitropyridin-3-yl-N-oxide)-2-butenoate

A solution of 5.0 g (0.027 m) methyl 3-[(2,3-dihydroxypropyl)amino]-2-butenoate, 3.03 g (0.03 m) triethylamine, and 4.74 g (0.03 m) 3-fluoro-4-nitropyridine-N-oxide in 60 ml isopropanol is heated at 50° for 3 days. The solvent is removed on the rotary evaporator and the residue is subjected to flash chromatography on silica gel with elution by 10% methanol/chloroform. The material with $R_f=0.5$ is collected. The desired product is a brownish solid with m.p. 65°–70°.

EXAMPLE 2

Substituted 4-nitropyridine-N-oxide

When the procedure of Example 1 is repeated but substituting a stoichiometrically equivalent amount of the ester reactants listed below the correspondingly substituted 4-nitro pyridine oxide shown below is obtained.

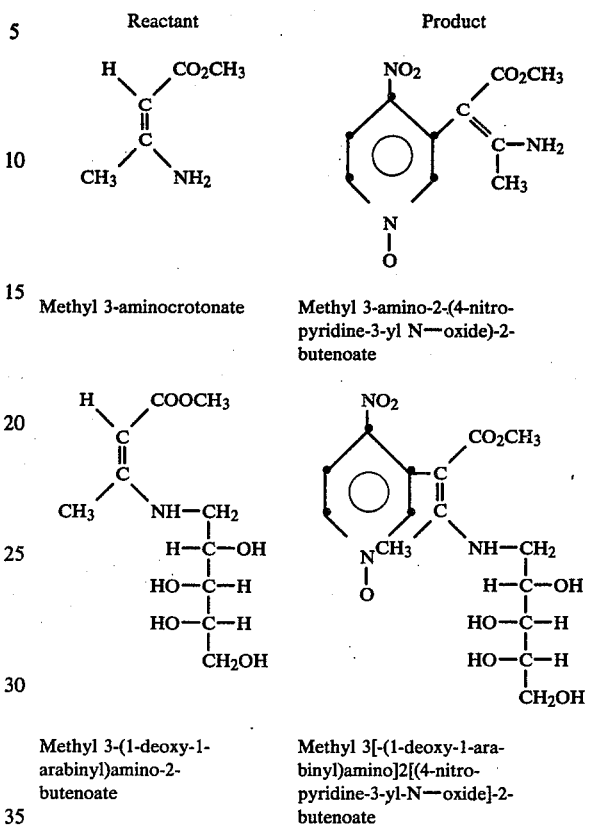

EXAMPLE 3

Sterile Isotonic Solutions for Injection

Suitable formulations for injection are prepared by dissolving each of the compounds of Examples 1 and 2 inclusive in isotonic solution in a concentration of about 1 mg/ml and sterilizing the resulting solution. It is suitable for intravenous injection.

EXAMPLE 4

Capsules

Suitable formulations for oral administration are prepared by filling appropriately sized capsules individually with 25 and 50 mg portions of each of the compounds produced in accordance with Examples 1–2 inclusive.

EXAMPLE 5

| Tablet Formulation | |
|---|---|
| Ingredients | Amount |
| Product of Examples 1–2 | 25 mg |
| Calcium phosphate | 120 mg |
| Lactose | 50 mg |
| Starch | 23 mg |
| Magnesium Stearate | 1 mg |

What is claimed is:

1. A 4-nitropyridine-N-oxide of the formula

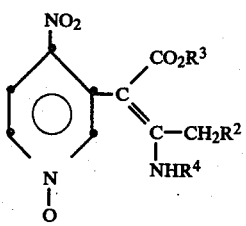

wherein $R^2$ and $R^3$ are each selected from hydrogen, loweralkyl, hydroxyloweralkyl, and loweralkoxylower alkyl;

$R^4$ is selected from hydrogen, lower alkyl, hydroxyl- loweralkyl and loweralkoxylloweralkyl.

2. A compound according to claim 1 which consists of methyl [3-(2,3-dihydroxypropyl)amino-2-(4-nitropyridin-3-yl-N-oxide)]-2-butenoate.

3. A process for the preparation of the compound of claim 1 which comprises contacting 3-fluoro 4-nitropyridine-N-oxide with an alkenoate ester of the formula

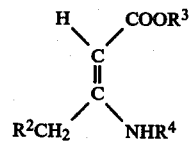

4. A method of enhancing the therapeutic effect of radiation which comprises administering to a patient in need of such radiation treatment an effective amount of a compound of the formula

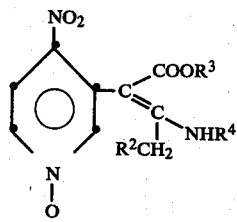

wherein $R^2$ and $R^3$ are each selected from hydrogen, loweralkyl, hydroxyloweralkyl and alkoxyloweralkyl lower $R^4$ is selected from hydrogen, loweralkyl, hydroxyl- loweralkyl, and lower alkoxylloweralkyl.

5. A pharmaceutical composition for enhancing the therapeutic value of radiation which consists of an effective amount of the compound of claim 1 and a non-toxic pharmaceutically acceptable carrier.

* * * * *